United States Patent [19]

Smith

[11] 4,042,685
[45] Aug. 16, 1977

[54] MILK OF MAGNESIA

[76] Inventor: Walton John Smith, P.O. Box 461, Wilton, Conn. 06897

[21] Appl. No.: 615,507

[22] Filed: Sept. 22, 1975

Related U.S. Application Data

[63] Continuation of Ser. No. 470,026, May 15, 1974, abandoned, which is a continuation-in-part of Ser. No. 301,596, Oct. 27, 1972, abandoned, and Ser. No. 131,559, April 5, 1971, abandoned.

[51] Int. Cl.$^2$ .............................................. A61K 33/08
[52] U.S. Cl. .................................... 424/158; 424/147; 424/230
[58] Field of Search .............................. 424/157, 158

[56] References Cited

U.S. PATENT DOCUMENTS

| 2,052,902 | 9/1936 | Snyder | 424/158 |
|---|---|---|---|
| 2,755,220 | 7/1956 | Alford et al. | 424/158 |
| 2,843,521 | 7/1958 | Entrekin | 424/157 |
| 2,908,614 | 10/1959 | Muggleton et al. | 424/87 |
| 3,347,744 | 10/1967 | Latshaw | 424/157 |
| 3,369,968 | 2/1968 | Smith | 424/157 |

OTHER PUBLICATIONS

*Remington's Practice of Pharmacy*, 12th Ed. (1961), Mack Pub. Co., Easton, Pa. pp. 153–157.

*Primary Examiner*—Frederick E. Waddell
*Attorney, Agent, or Firm*—Larson, Taylor and Hinds

[57] ABSTRACT

An improved form of milk of magnesia, dispensable as a solid, is prepared by combining magnesia magma with a water soluble carbohydrate followed by desiccation. The soluble carbohydrate prevents magnesium hydroxide particles from being entrained in the water vapor during the desiccation process and also permits the dried product to reform a colloidal suspension on the addition of water. The desiccated milk of magnesia composition can be flavored with a wide variety of normally alkali-sensitive flavoring agents by incorporating suitable edible acids in the mixture prior to desiccation.

4 Claims, No Drawings

MILK OF MAGNESIA

This application is a continuation of my application Ser. No. 470,026, filed May 15, 1974, now abandoned, which is a continuation-in-part of application Ser. No. 131,559, filed Apr. 5, 1971, now abandoned, and application Ser. No. 301,596, filed Oct. 27, 1972, now abandoned.

This invention pertains to improvements in antacids and laxative preparations formed from insoluble inorganic materials. More particularly, the present invention pertains to an improved milk of magnesia product and methods of preparing that product.

An aqueous suspension of magnesium hydroxide, better known as milk of magnesia, is a well-known and highly effective antacid and laxative which has been in commercial use for decades. Despite the recognized value of this product and the long period of time in which it has been available, there are several long-standing and significant problems associated with the production and use of milk of magnesia which have remained unsolved.

As presently available commercially, milk of magnesia is usually prepared by diluting magnesia magma, a colloidal suspension of magnesium hydroxide containing about thirty percent (30%) magnesium hydroxide to an ultimately packaged product which contains less than ten percent (10%) solids, the remainder being substantially water. The sale of milk of magnesia in liquid form has several advantages. The product is bulky and heavy thereby increasing shipping costs and requiring the use of larger and more expensive packages than would be necessary if the product were prepared and shipped in a more concentrated form such as a solid. The bulk and weight of the product also constitutes a serious limitation on its portability by the user since it is inconvenient to carry the product on one's person or in handbags. Finally, the therapeutic value of the product may be impaired if it becomes frozen since the colloidal suspension of relatively insoluble magnesium hydroxide does not readily reform upon thawing.

A second significant problem associated with commercially available milk of magnesia is its unpleasant and chalky taste. This problem is particularly troublesome since milk of magnesia is often prescribed for children. Although peppermint flavored milk of magnesia is available, a large number of commercially available flavoring agents are alkali-sensitive and, therefore, have limited shelf life when incorporated in the highly alkaline milk of magnesia suspension.

Such prior art attempts as have been made to form a solid milk of magnesia product have not been totally successful. For example, U.S. Pat. No. 2,052,902 describes the preparation of a solid milk of magnesia containing colloidal clays which are added to the product to enhance its ability to reform a colloidal suspension upon the addition of water after drying. The use of colloidal clays is less than desirable since they have an adverse effect on the already poor taste and chalky consistency of milk of magnesia, U.S. Pat. No. 3,369,968 describes a freeze-dried solid milk of magnesia product. While solid milk of magnesia can be formed by freeze-drying techniques, as described in that patent, such a product is not entirely satisfactory from a commercial standpoint due to product losses occasioned by entrainment of fine magnesium hydroxide particles in the water vapor during freeze or spray drying. Moreover, the freeze-dried product described in the aforementioned patent does not overcome the taste problem associated with milk of magnesia.

It is an object of the present invention to provide an improved, commercially acceptable, solid milk of magnesia product and a method of forming such a product.

It is another object of the present invention to provide a solid milk of magnesia product which will readily reform to a colloidal suspension of milk of magnesia upon the addition of water.

Yet another object of the present invention is to provide a flavored solid milk of magnesia product in a wide variety of normally alkaline-sensitive flavors.

Further objects of the invention are to provide a novel method for the production of freeze-dried or spray-dried milk of magnesia which does not result in extensive loss of solids during manufacture; produces a product which is capable of reforming a colloidal suspension of magnesium hyroxide upon the addition of water; permits the addition of flavoring agents to the product; overcomes chalky taste; and has no adverse effect upon shelf life; all without substantial increase in cost.

It has now been discovered that a solid milk of magnesia which will reform to a colloidal suspension upon the addition of water or other edible liquids, can be prepared by the addition of soluble materials to magnesia magma or other colloidal suspension of magnesium hydroxide prior to converting the suspension to a solid. It has also been discovered that the soluble materials are particularly useful in the production of solid freeze- or spray-dried milk of magnesia, the preferred composition of the invention, since the use of these materials prevents the entrainment of fine magnesium hydroxide particles in the water vapor drawn off during the drying step associated with freeze- or spray-drying processes. A further feature of the invention is the discovery that by incorporating suitable edible acids in the magnesium hydroxide suspension prior to forming the solid milk of magnesia product by freeze-drying or spray-drying techniques, it is possible to employ a wide variety of flavoring agents, including normally alkaline sensitive agents, and to thereby produce a milk of magnesia product having greater palatability.

The soluble materials which have been discovered to be useful in the production of solid milk of magnesia via freeze-drying or spray-drying processes possess several significant characteristics. In addition to being soluble, the materials are edible; they should not have an adverse effect on the flavor of the product and preferably be flavor enhancers; and be solids at normal temperature. Further, materials having relatively higher molecular weight are preferred to lower molecular weight materials since the lower molecular weight materials have a greater depressant effect on the freezing point and are generally more hygroscopic, thereby increasing the cost of freezing and impairing the shelf life of the solid product. The preferred soluble materials of this invention are water soluble carbohydrates such as di-, and poly-saccharides or mixtures thereof. Typical soluble carbohydrates which may be employed include maltose, dextrose, lactose, sugar (sucrose) and hydrolyzed starch. Of these, sugar (sucrose) and hydrolyzed starch are preferred, the latter being especially advantageous, because of higher molecular weight and ability to enhance the flavor of the final product. As used herein the term "hydrolyzed starch" is intended to define a carbohydrate intermediate lying between starch and the sugars, sometimes denominated dextrin, and produced from starch by hydrolysis. A readily available hydrolyzed starch is that sold under the name Maltrin 10 from Grain Processing Company, Muscatine, Iowa whose composition is about 84% penta- and higher saccharides and 16% tetra- and lower saccharides.

The amount of soluble carbohydrate which is added to the magnesia magma or colloidal suspension of magnesium hydroxide is not critical. Acceptable products can be made by employing an equal part, by dry weight of magnesium hydroxide present in said suspension, of the soluble carbohydrate or as much as three times or more by weight of the dry magnesium hydroxide. It is a rather surprising feature of the invention that the addition of large quantities of soluble carbohydrate to the magnesia magma does not increase the viscosity of the mixture or make it more difficult to obtain a homogeneous mixture for further processing to form the final solid product.

In accordance with method aspects of the invention, magnesia magma is combined with the soluble carbohydrate and thoroughly mixed to obtain a uniform mixture. Water may be added to the magma-carbohydrate mixture to facilitate the formation of a uniform mixture which is desirable to insure uniformity of the final solid product. The mixture is then subjected to desiccation using freeze-drying or spray-drying processes. Such processes are well known in the art. In the typical freeze-drying process, the mixture of magnesia magma, soluble carbohydrate and other additional ingredients, if any, as will be described more fully hereinafter, is rapidly frozen to assure uniformity in the final product. Ordinarily, this is accomplished by pouring the mixture to be frozen into trays, the thickness of the layer in each tray being controlled so that rapid and uniform freezing is achieved. Thereafter, the frozen material is dried in a vacuum chamber at low absolute pressure.

In a typical spray-drying process, the uniform mixture of magnesia magma and additives is sprayed into a vacuum chamber where it is dehydrated by a current of warm air which entrains the moist vapors, and the dried material is collected as a fine powder.

As previously pointed out, a wide variety of flavoring agents including cocoa, strawberry, banana, lemon and even fresh fruits may be incorporated in the magnesia magma-carbohydrate mixture prior to further processing to the solid state. The resultant final solid product gives rise to an enhanced flavor when reconstituted with water or other edible liquid. It has heretofore not been thought possible to utilize a wide range of flavoring agents with milk of magnesia since many flavoring agents are formed from esters which are readily hydrolyzed when exposed to an alkaline media. Milk of magnesia is, of course, highly alkaline having a pH in the range of 10–11. The alkalinity of milk of magnesia may be adjusted by the addition of small quantities of suitable edible acids to the magnesia magma-soluble carbohydrate mixture along with the flavoring agent prior to the desiccation process. Because of the relative insolubility of magnesium hydroxide in water, the addition of relatively small amounts of edible acid ranging from about 0.10 parts to 0.03 or more parts of acid per part of dry magnesium hydroxide to the mixture will pose the pH of the mixture to near neutrality. The addition of flavoring and acidulating agents followed by immediate freeze- or spray-drying has been found to preserve the flavor. Moreover, since the solid milk of magnesia will not be reformed into a colloidal suspension until immediately prior to its consumption the alkalinity problem is avoided and the flavor retained and enjoyed by the consumer.

The selection of a suitable edible acid is not critical to the invention and a wide variety of edible organic acids may be employed. Typical acids include maleic, tartaric, fumaric, adipic and, preferably, citric acid.

A variety of additional substances may be added to the magma mixture prior to the desiccation process. For example, artificial sweetners such as saccharin may be employed to further enhance the flavor of the final product. Similarly, thickening agents such as milk powders, cellulosic materials, including microcrystalline cellulose, carageenin and sodium caseinate may be incorporated in order to enhance the stability of the colloidal suspension of the reconstituted milk of magnesia product. The addition of other known materials which may enhance the flavor, or therapeutic value of the product, e.g. defoaming silicones, may also be employd.

The invention will be further understood by reference to the following illustrative examples. In these examples, the mixture was frozen in a dry ice-acetone mixture.

EXAMPLE I 100 grams of magnesia magma containing about 30 parts of magnesium hydroxide was mixed with 100 grams of water until a uniform mixture was obtained. To this mixture was added 30 grams of sugar, 1 gram of citric acid, 500 mg. of calcium saccharin, 250 mg. of F D & C yellow No. 5, and 1 cc. of lemon oil. The mixture frozen in a dry ice-acetone bath and subsequently dried in a vacuum chamber until completely dry. The final product was a solid milk of magnesia composition which was uniform and readily reconstituted upon the addition of water to form a lemon flavored colloidal suspension.

EXAMPLE 2

100 grams of magnesia magma are mixed with 100 grams of water until uniform. Thereafter, 30 grams of sugar and 1 gram of citric acid with an additional 100 grams of water are added and mixed. In a separate vessel, 25 grams of cocoa, 70 grams of sugar and 100 grams of water are combined. When this latter mixture is uniform, it is added with stirring to the magnesia mixture until it is uniformly mixed and is then poured into the vessel in which it is to be freeze-dried. The resulting product readily forms a colloidal suspension of milk of magnesia upon the addition of water and has an excellent chocolate taste.

EXAMPLE 3

The procedure of Example 1 is repeated using lactose instead of sugar. The final product after freeze-drying was comparable to the product made with sugar.

EXAMPLE 4

Example 1 is repeated using Maltrin 10 instead of sugar. The final product was easily reconstituted with water.

EXAMPLE 5

Example 1 is repeated using 30 grams of Maltrin 10 in addition to 30 grams of sugar. The resulting product was superior to the products formed in Example 1 and Example 4 in case of reconstitution.

EXAMPLE 6

The milk of magnesia mixture of Example 2 was spray-dried in lieu of freeze drying. The resultant spray-dried product formed a colloidal suspension of milk of magnesia upon addition of water.

EXAMPLE 7

Example 4 is repeated with the exception that bismuth subsalicylate magma is substituted for magnesia magma.

EXAMPLE 8

| Ingredient | Amount in lbs. |
| --- | --- |
| Magnesia magma | 100 |
| Sugar | 30 |
| Maltrin 10 (hydrolyzed starch) | 44 |
| Water | 100 |

The magnesia magma is diluted with the water and to this is added the sugar and the Maltrin 10 with stirring. Advantageously, non-shearing mixing is used. Should the mixture appear to contain any large particles, screening of the mixture may be undertaken. The mixture is subjected to freeze-drying to produce solid particles which upon addition of water produce colloidal milk of magnesia.

Various modifications of the invention disclosed herein will be readily occur to persons skilled in the art. For example, the solid milk of magnesia may be reconstituted with milk in lieu of water or may be tabletted for chewing. It will also be evident to those persons skilled in the art that the methods disclosed herein will be equally applicable to the formation of freeze- or spray-dried products from other well known magmas such as aluminum or iron hydroxide or bismuth subsalicylate.

What is claimed is:

1. An article of manufacture comprising a desiccated mixture of magnesium hydroxide magma and dextrin in an amount of from 1 to 3 parts by weight per part of magnesium hydroxide in said magma, said desiccated mixture being produced by spray or freeze drying.

2. The article of claim 1 containing citric acid in an amount of from 0.01 to 0.03 parts by weight per part of magnesium hydroxide.

3. The article of claim 1 containing sugar.

4. The article of claim 2 containing lemon oil as a flavoring agent.

* * * * *